(12) United States Patent
Ehrenkranz

(10) Patent No.: US 6,448,232 B1
(45) Date of Patent: Sep. 10, 2002

(54) METHOD OF USING DIHYDROCHALCONE DERIVATIVES TO BLOCK GLUCOSE TRANSFER

(76) Inventor: Joel R. L. Ehrenkranz, 0101 Oakridge Dr., Aspen, CO (US) 81611

( * ) Notice: Subject to any disclaimer, the term of this patent is extended or adjusted under 35 U.S.C. 154(b) by 0 days.

(21) Appl. No.: 09/638,610

(22) Filed: Aug. 15, 2000

Related U.S. Application Data

(60) Provisional application No. 60/151,171, filed on Aug. 27, 1999.

(51) Int. Cl.[7] ............................................... A61K 31/70
(52) U.S. Cl. ....................................................... 514/25
(58) Field of Search ............................................ 514/25

(56) References Cited

U.S. PATENT DOCUMENTS

| | | | |
|---|---|---|---|
| 4,760,155 A | 7/1988 | Diedrich et al. |
| 4,840,939 A | 6/1989 | Leveen et al. |
| 4,959,355 A | 9/1990 | Fishbarg et al. |
| 5,424,406 A | 6/1995 | Tsujihara et al. |
| 5,731,242 A | 3/1998 | Tsujihara et al. |
| 5,767,094 A | 6/1998 | Tsujihara et al. |

OTHER PUBLICATIONS

F.H. Riley et al Phlorhizin Diabetes in Dogs American J. Physiology 1:395, 410, 1989.

*Primary Examiner*—Elli Peselev
(74) *Attorney, Agent, or Firm*—Berud W. Sandt

(57) ABSTRACT

A method for the oral administration of dihydrochalcones to inhibit glucose absorption.

8 Claims, No Drawings

METHOD OF USING DIHYDROCHALCONE DERIVATIVES TO BLOCK GLUCOSE TRANSFER

This application is a continuation-in-part of provisional application No. 60/151,171 filed Aug. 27, 1999.

The present invention relates to a method for the use of dihyrochalcone derivatives and specifically phlorizin and derivatives thereof to block the intestinal absorption of glucose and renal tubule resorption of glucose in mammals and thereby provides a method for the treatment of obesity and diabetes.

BACKGROUND

It is known that the subcutaneous administration of phlorizin causes inhibition of the sugar transport process through intestinal and renal cell walls in mammals and thereby decreases the level of glucose in the bloodstream and promotes the excretion of glucose (e.g., Journal of Clinical Investigation, 79, p. 1510 (1987), ibid., 80, 1037, (1987), ibid., 87, p.561 (1990). Specifically, phlorizin is known to inhibit the sodium glucose symporter, an enzyme transport system found in the small intestine that is used to transport glucose across intestinal epithelium, and in the renal tubule, where the enzyme transports sodium, lithium and glucose from the tubule into the renal vasculature. By blocking the action of this enzyme, phlorizin prevents intestinal absorption of glucose and the renal resorption of glucose. Consequently dihydrochalcones, such as phlorizin, can be used to reduce obesity and lower the intake of insulin in diabetic mammals.

It has also been stated in a number of publication that the oral administration of phlorizin, although effective as glucose transport inhibitor through intestinal and kidney cells, is not useful because toxic effects, which are in part attributed to the formation of phloretin, the hydrolysis product of phlorizin in the intestines. As a result a number of phlorizin and phloretin derivatives have been developed which have been asserted as avoiding the toxic effect of particularly phloretin (U.S. Pat. Nos. 4,760,135, 5,731,292 and 5,767,094).

SUMMARY OF THE INVENTION

It is an object of the present invention to provide a method for the oral administration of dihydrochalcones to inhibit the renal tubular glucose absorption, and/or inhibit the absorption of glucose at the intestine, under conditions, which reduce the formation of toxic byproducts. It is another object to provide a method to block the postprandial rise in blood glucose. Another object is to provide a method for the treatment of acute glucose toxicity and to correct hyperglycemia. The present invention also provides a method for blocking the uptake of glycosylated drugs and hormones into cells and to increase their renal excretion. It also involves a method to increase sodium and lithium excretion from the body as a method for the treatment of lithium toxicity. It has also been discovered that dihydrochalcone derivatives are useful in preventing hypoglycemia. Additionally the present invention provides a weight loss method.

These and other objects are accomplished by orally administering a dihydrochalcone derivative in multidoses on a daily basis at a time when the intestine is relatively uninvolved in the digestion of food. The dihydrochalcones preferably used are phlorizin and derivatives of phlorizin which inhibit the transfer of glucose through the walls of intestinal and renal cells.

DETAILED DESCRIPTION OF THE INVENTION

The present invention comprises orally administering dihydrochalcone derivatives to mammals on a daily multidose basis at a time when the intestinal tract of the mammal is at a low point in its gastric activity, e.g. on an empty stomach. The dihydrochalcone derivatives employed in the present invention include specifically phlorizin and derivatives of phlorizin which are able to inhibit the transfer of glucose. The number of doses administered and the amount of the dihydrochalcone derivative in each dose will of course vary with the mammal, the derivative and the effect desired, but should be at least three times daily and should contain at least 10 mg/kg of body weight. Similarly the optimum time to administer the derivative will vary but preferably is 90 to 30 minutes before food is consumed assuming regular dietary habits. The actual conditions and concentrations under which the derivative is administered can be best established experimentally by measuring the increase in the glucose content in urine or the decrease of glucose in the blood stream after having established the desired degree of inhibition.

The preferred dihydrochalcone compounds employed in the procedure of the present invention are dihydrochalcone glycosides such as phlorizin and alkoxy, alkyl- and aryl amine substituted phlorizins where the substituents can be either on the glycoside moiety or on the dihydrochalcone moiety, provided not more than one hydroxyl group in the dihydrochalcone moiety and not more than two hydroxyl groups in the glycoside moiety have been replaced by the stated substituents. In general the procedure of the present invention is most effective with phlorizin itself although improved blocking of glucose transport is also obtained with other phlorizin derivatives using the procedure of the present invention.

Phlorizin itself is a well-known pharmaceutical ingredient that is obtained from the bark of apple trees. Although it has been known to be useful, particularly through subcutaneous administration, as a method to study the cellular transport of glucose, it has not found acceptance because of the belief that phlorizin exhibits toxic side effects. As a result derivatives of phlorizin have been developed which are asserted not to exhibit such side effects, e.g., U.S. Pat. Nos. 4,760,135, 5,767,094 and 5,731,292. However, these derivatives are not seen to be totally satisfactory when used under the conditions described in the literature. The present invention is based on the discovery that the oral administration of phlorizin on an empty stomach allows the use of lower concentrations of phlorizin at levels which do not appear to have a toxic effect on the operation of key organs such as the pancreas or brain, which is indicative of toxic effects on the mammal as a whole. Although I do not wish to be bound by such it is my belief that the reason for the ability to use phlorizin without toxic side effect is the ability to reduce the hydrolysis of the phlorizin to a minimum.

The dihydrochalcone glycosides employed in the present invention may be administered in dry powder, tablet, capsule or aqueous or other suitable form. The material however should not be ingested with food products, which stimulate gastric activity or compete with phlorizin for intestinal absorption. The dose will vary depending on the conditions of patients and the severity of the condition to be ameliorated. The phlorizin compound should be administered at least three times daily and not more than five times to coincide with conditions of low gastric and intestinal activity. The amount of the phlorizin compound in each dose should be at least 10 mg/kg of body weight. It can be increased but should not exceed 50 mg/kg of body weight in order to avoid toxic effects.

The invention is further illustrated by the following examples, which are only demonstrative and not intended to limit the scope of the present invention.

EXAMPLE 1

1 gm. phlorizin (Sigma Chemical Company) was taken orally by a 85 kg male either as a dry powder in a or in the form of a solution in milk on an empty stomach. The glucose concentration in urine was measured after ingestion and showed the following results.

| time after phlorizin ingestion | urine glucose |
|---|---|
| 0 minutes | no food: <50 mg/dl in milk: <50 mg/dl |
| 90 minutes | no food: 500 mg/dl in milk: <50 mg/dl |
| 150 minutes | no food: 50 mg/dl in milk: <50 mg/dl |
| 210 minutes | no food: <50 mg/dl in milk: <50 mg/dl |

The data show that at the concentrations employed phlorizin is effective as a glucose blocker only if it is ingested without food on an empty stomach.

EXAMPLE 2

1.5 grams phlorizin as a dry powder in a gelatin capsule was ingested orally three times a day, 90 minutes before eating on an empty stomach. Weight measured at the same time each day with a digital electronic scale. Normal dietary conditions were maintained during the time that the phlorizin was ingested.

| Experiment | Weight |
|---|---|
| Experiment 1 | |
| Pre-phlorizin weight | 192.2 lbs. |
| Weight after 3 days of phlorizin | 189.4 lbs. |
| Experiment 2 | |
| Pre-phlorizin weight | 193.2 lbs. |
| Weight after 3 days of phlorizin | 185.4 lbs. |
| Experiment 3 | |
| Pre-phlorizin weight | 191.5 lbs. |
| Weight after 3 days of phlorizin | 186.8 lbs. |
| Experiment 4 | |
| Pre-phlorizin weight | 194.4 lbs. |
| Weight after 3 days of phlorizin | 189.0 lbs. |

EXAMPLE 3

1.5 g of phlorizin as a dry powder in a gelatin capsule was ingested one hour prior to ingesting 100 g of carbohydrates and compared to similar ingestion of carbohydrates without the prior consumption of the phlorizin. Glucose and insulin levels were measured just prior to and 30 and 60 minutes following carbohydrate ingestion and glucose levels were also measured 90 and 120 minutes after carbohydrate ingestion. Glucose levels were established by glucose oxidase reaction using whole blood and measuring the color generated with a hand-held spectrophotometer. Serum insulin was measured using commercially available immunoassay devices and methods.

| | GLUCOSE (in mg/dl) | | INSULIN (in microIU/ml) | |
|---|---|---|---|---|
| | With phlorizin | Without phlorizin | With Phlorizin | Without phlorizin |
| 0 minutes | 90 | 118 | 5 | 9 |
| 30 minutes | 146 | 178 | 34 | 60 |
| 60 minutes | 144 | 99 | 28 | 61 |
| 90 minutes | 108 | 67 | | |
| 120 minutes | 117 | 89 | | |

These data demonstrate the phlorizin is able to decrease the postpandrial rise in glucose and insulin levels and hence demonstrates that phlorizin is useful for the treatment of diabetes, as it lowers glucose and insulin levels. The data also show that phlorizin is effective in preventing reactive hypoglycemia as can be seen from comparing the glucose levels at 90 and 120 minutes with and without phlorizin treatment showing that treatment with phlorizin prevented the fall in blood glucose levels below the o minute value.

The foregoing results show that phlorizin is effective in reducing body weight.

What is claimed is:

1. A method of blocking glucose transport across cell walls in mammals consisting essentially of orally administering to said mammals from 10 to 50 mg/kg of body weight of phlorizin within 120 minutes before the ingestion of food.

2. The method of claim 1 wherein the mammal is a human.

3. The method of claim 2 wherein the phlorizin is used to cause weight loss.

4. The method of claim 2 wherein the phlorizin is used to lower blood glucose.

5. The method of claim 2 wherein the phlorizin is used to treat hyperglycemia, glucose toxicity or diabetes mellitus.

6. The method of claim 2 wherein the phlorizin is used to increase sodium and lithium excretion from the body.

7. The method of claim 2 wherein the phlorizin is used to treat lithium toxicity.

8. The method of claim 2 wherein the phlorizin is used to treat reactive hypoglycemia.

\* \* \* \* \*